(12) United States Patent
Bowles et al.

(10) Patent No.: US 6,485,417 B1
(45) Date of Patent: Nov. 26, 2002

(54) ALZHEIMER'S TESTER

(75) Inventors: Henry M. Bowles, Alameda; Theodore D. Langley, San Francisco, both of CA (US)

(73) Assignee: Bowles-Langley Technology, Inc., Alameda, CA (US)

( * ) Notice: Subject to any disclaimer, the term of this patent is extended or adjusted under 35 U.S.C. 154(b) by 0 days.

(21) Appl. No.: 09/637,474

(22) Filed: Aug. 11, 2000

Related U.S. Application Data

(63) Continuation-in-part of application No. 09/053,111, filed on Apr. 1, 1998, now Pat. No. 6,113,538.
(60) Provisional application No. 60/058,841, filed on Sep. 15, 1997.

(51) Int. Cl.[7] .................................................. A61B 5/00
(52) U.S. Cl. ...................................................... 600/300
(58) Field of Search ................................. 600/300, 301, 600/558, 544; 128/925; 434/258, 118, 219, 236; 273/454; 340/576; 345/904

(56) References Cited

U.S. PATENT DOCUMENTS

| | | | |
|---|---|---|---|
| 5,295,491 A | * | 3/1994 | Gevins ........................ 600/544 |
| 5,344,324 A | * | 9/1994 | O'Donnell et al. .......... 600/558 |
| 5,724,983 A | * | 3/1998 | Selker et al. ................ 600/301 |
| 5,778,893 A | | 7/1998 | Potter |
| 6,113,538 A | * | 9/2000 | Bowles et al. ............... 600/300 |

* cited by examiner

*Primary Examiner*—Kevin Shaver
*Assistant Examiner*—Brian Szmal
(74) *Attorney, Agent, or Firm*—Crosby, Heafey, Roach & May; John Carpenter

(57) ABSTRACT

A computer is provided along with a method for testing users for alertness and mental fitness. The system and method are usable wherever there is a risk to persons, property, or the environment from individuals not fit to operate machinery or enter an work area safely, or for testing a user for dementia or other neurological impairment. The testing methods resemble computer games, but they actually measure mental fitness and alertness rather than aptitude, ability, or intelligence. The disclosed basic test is general, simple and non-intellectual, and compatible with worldwide, multilingual use. Other tests are more specifically designed to test for the ability to perform certain occupational duties or types of activities. Tests which measure neurological impairment do involve some intellectual functions such as memory. The basic test preferably comprises a plurality of yes or no questions based upon graphical data displayed to the user. Each user's answers and performance are preferably maintained in strict confidence through storage only on a removable storage medium, such as a Smart Card. Some neurological tests, such as for Parkinson's disease, may entail measuring finger tremors.

48 Claims, 1 Drawing Sheet

ALZHEIMER'S TESTER

CROSS-REFERENCE TO RELATED APPLICATIONS

This application claims priority from U.S. patent application Ser. No. 09/053,111, entitled Alertness Tester, filed Apr. 1, 1998, now U.S. Pat. No. 6,113,538, which is incorporated herein by reference. Also incorporated herein by reference is U.S. Provisional Patent Application Serial No. 60/058,841, entitled Brain Function Tester for All Ages, filed Sep. 15, 1997. Also incorporated herein by reference are the following disclosure documents filed with the U.S. Patent and Trademark Office: U.S. Pat. No. 394,198, entitled Special Purpose Computer System for Alertness and Readiness Testing, filed Mar. 4, 1996; U.S. Pat. No. 383,562, entitled Multilingual Software and its Use in Dedicated Computer System Used for Alertness and Readiness Testing, filed Mar. 11, 1996; U.S. Pat. No. 399,622, entitled Software and Hardware System to Test Alertness and Fitness, filed Jun. 6, 1996; U.S. Pat. No. 405,957, entitled Nonlinguistic Turnkey Test System for Mental Alertness and Awakeness, filed Oct. 16, 1996; U.S. Pat. No. 422,723, entitled Alertness Testing System with Alertness Gauge, filed Aug. 6, 1997; and U.S. Pat. No. 423,524, entitled Medical, Visual and Psychomotor Testing System, filed Aug. 21, 1997.

FIELD OF THE INVENTION

The present invention relates generally to the field of Alzheimer's testing, and more specifically to a system for implementing non-linguistic testing procedures for establishing and remotely recording a baseline level of mental function capability intended for comparison to a given test result.

BACKGROUND OF THE INVENTION

Accidents in the workplace cost society many billions of dollars, hundreds of lives and cause considerable damage to the environment each year. The majority of these accidents are caused by human error. Human error has, of course, many causes, but it is most prevalent when an operator is impaired from lack of sleep, illness, or is under the influence of drugs or alcohol. In the U.S., at least 7.5 million workers in high-risk occupations are required to take random blood or urine tests to deter the use of drugs and alcohol on the job, a requirement which has helped reduce accidents. However, fatigue, illness and stress are more common causes of impairment than are the effects of drugs or alcohol. Accidents continue to occur in large part because workers are impaired by illness, exhaustion, stress, side-effects from prescription medications or from a combination of these factors. There is therefore an urgent need for a way to screen workers for all impairment factors and causes before they begin work. Such screening should be sensitive to impairment regardless of its cause, should provide results individualized for the user, should be simple and quick to use, and should insure the maintenance of worker privacy.

As for illness affecting performance, with an aging population and older workers than in the past, Alzheimer's disease may pose a significant workplace performance factor as well. A reliable, simple to use Alzheimer's test would therefore contribute to workplace safety. Moreover, a test for Alzheimer's would also be useful for those who do not work, since the progress of the disease can be slowed or arrested by treatment if it is detected and treated early. Medical experts estimate that there are over four million persons afflicted with Alzheimer's disease in the U.S. alone. This number is expected to increase annually because of the increasingly greater percentage of the population over 55 years of age. Rates of occurrence for other diseases affecting mental performance, such as Parkinson's, are also expected to increase over the next ten years.

Currently, the two standard tests for Alzheimer's disease are the Mini Mental State Exam and the Janssen Seven Minute Screen. Both require fifteen minutes or more to administer and score, and both require administration by a trained nurse or technician. Since these tests must be administered in a doctor's office or in a clinic by a trained person, they are expensive and are therefore impractical for testing on a very large scale. Moreover, administration of the available tests is susceptible to the administrator's personal biases and influence, and the results are not private, or at least are susceptible to a breach of privacy. Also, available Alzheimer's tests cannot be used for mass screening in public places where a trained professional to help administer the test is unavailable.

The present invention permits mass testing for Alzheimer's disease, as well as for Parkinson's Disease and other neurological impairments, in an objective manner, while maintaining each person's privacy by recording their scores on their own personal datacard. The inventive tests and mechanism for their administration provides for standardization of tests and results, for individuals or across groups, and can be administered in pharmacy chains and senior centers for inexpensive mass screening of the general population.

SUMMARY OF THE INVENTION

The present invention addresses these concerns with a reliable and economical test for Alzheimer's Disease or other dementia and for general alertness with a tester which is easy to use and protects user privacy. The inventive tester preferably comprises a compact, single-purpose computer which can be hung on a wall, placed on a table, installed in a booth, or mounted in an instrument panel. The inventive tester provides a standard for checking worker alertness, or a person's risk or progress of Alzheimer's, which can be utilized throughout an industry, medical facility, or among entities nationally and internationally. For dementia and related disease testing, the invention specifically includes a method to administer a mental function test (including standardized tests) for medical use utilizing a tester. The invention therefore enables early Alzheimer's disease detection, thereby enabling early treatment and increasing the chances of recovery or arresting the progress of the disease.

The present invention therefore comprises a system to assess a user's level of alertness or mental fitness by using computer-delivered tests and a personal data device (preferably a Smart Card, but referred to herein generally as a datacard). In workplace testing, the datacard can be adapted to permit or prevent use of or access to equipment or work areas, depending on the person's level of alertness. In dementia testing, the datacard records individual longitudinal profile data about risk or current status of dementia, such as Alzheimer's disease. The tester preferably maintains personal privacy by retaining test performance and baseline information only on each user's own datacard, which each user carries as personal property. Preferably, no personal data is retained in any computer, database or tester. Personal data are retained only on a user's own datacard, thereby maintaining user privacy. Each user's own personal level of test performance is coded into the user's own datacard.

When a test ends, any performance data retained by the tester memory is preferably automatically erased.

It is therefore an advantage of the present invention to provide a system and method for testing for alertness or risk of dementia in a user, the system comprising, a microprocessor, a visual display apparatus in electrical communication with the microprocessor, a data input/output ("I/O") port in electrical communication with the microprocessor, a portable data storage device having a user data memory, the portable data storage device being releasably interfaceable with the data I/O port, thereby enabling data downloading to and data uploading from the microprocessor, a test memory in electrical communication with the microprocessor, the test memory being loaded with at least one executable software program comprising an Alzheimer's or other dementia test and a baseline data set, the test comprising test information displayed on the visual display, an input mechanism in electrical communication with the microprocessor for receiving input data from the user in response to the test information displayed on the visual display, the microprocessor being enabled to execute said software program, receive the test information from the test memory, display the test information on the visual display, receive the input data from the user via the input mechanism, compare the input data to the baseline data set, assign either of a selected test performance-pass and a test performance-fail signal to the user depending upon the result of the comparison, and forward the selected signal to the portable data storage device.

The method includes the steps of determining a baseline mental function capability of a user, testing a current mental function capability of a user, comparing the current mental function capability of said user with the user's baseline mental function capability, and displaying a result of the comparison. The mental function capability, depending on the particular test, can be alertness, Alzheimer's Disease, Parkinson's Disease, or any other neurologic impairment, including brain tumors.

BRIEF DESCRIPTION OF THE DRAWINGS

The aforementioned advantages of the present invention, as well as additional advantages thereof, will be more fully understood hereinafter as a result of a detailed description of a preferred embodiment when taken in conjunction with the following drawing in which.

DETAILED DESCRIPTION OF A PREFERRED EMBODIMENT

Figure 1:
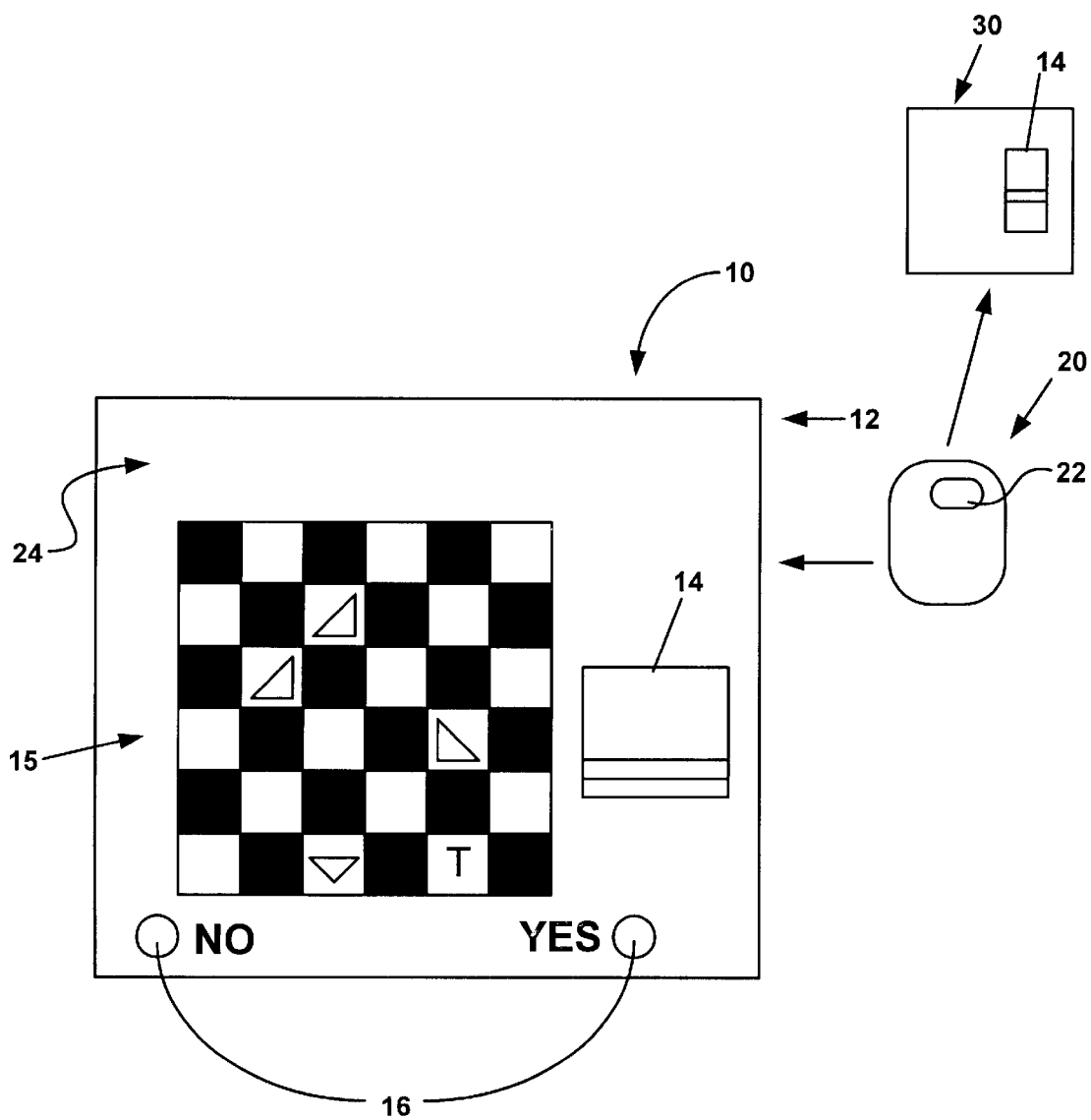
FIG. 1 illustrates a front view of a tester according to the present invention.

Referring to FIG. 1, alertness tester 10 of the present invention comprises a computer, preferably, but not necessarily, a single-use device, which calculates a user's score on a test and determines if the score is high enough to pass. A score must be at or near the user's baseline score to pass. If the user passes the test, then a pass code, plus the time and date, are written onto the user's ID card, referred to as a datacard 20.

A preferred test, implemented as software executable on the tester, preferably resembles a simple video game, and is completed quickly by a user (in about one minute, preferably less). In one embodiment, if a user performs particularly well on a given day, he or she preferably is provided an early exit and passing score after a shortened test period. A user's test result is preferably displayed on the screen before datacard 20 is removed, allowing the user to retake the test immediately if he or she failed to reach the established baseline or other passing score. Also, an appropriate message is preferably displayed before testing begins if the user's datacard is invalid, unreadable, or otherwise not properly functioning. An error message or symbol may also be provided on the display. All game materials, indicators, and feedback are preferably displayed to the user in the form of nonlinguistic, graphic symbols. The visual display may also include a gauge to graphically display the user's score relative to the user's baseline. The gauge may display the user's score relative to an absolute pass/fail line or relative to a range of passing or baseline scores, as per the system administrator's choice.

In one embodiment of the inventive test, the user decides whether a plurality of displayed figures (not shown) match by pressing YES or NO front panel buttons 16. Next to each button 16 is preferably a write-on area where a supervisor or test administrator can eraseably write "yes" and "no" in any language, as shown in FIG. 1 in English. NO and YES buttons 16 are preferably spaced far enough apart to allow users to use either one or both hands to respond. Also, the buttons are preferably large enough to be used while wearing gloves. An LED, capacitive, or other type of touch-sensitive screen may be utilized, as may a standard CRT display combined with external buttons.

A preferred enclosure 12 is either panel-mounted, tabletop, or wall-mounted, and approximately one foot square and about three inches deep, deeper if a standard CRT is utilized. However, flat screens and miniaturized components may be utilized to make an enclosure and tester of nearly any practical dimensions. Datacard reader 14 is preferably accessible by the user from the front or side. An electric power connector is preferably located on one of the edges or on the rear surface, but preferably not on the front. The system may also be battery operated or rely on solar power or some alternative power source understood by one skilled in the art to which the present invention pertains. It may also be small enough to be portable, even carried on one's person, carried in hand, strapped to an arm or wrist, or attached via a belt-clip. On front panel 24, there may also be a logo, company name, instructions and/or indicator lights.

The directions of primary data flow should be discussed to promote a better understanding of tester 10. First, user identity and, if available, baseline performance data is read when datacard 20 is first inserted into the tester. When a baseline is being established for a user, data is read from and written to the datacard. Once established, a baseline is preferably accessed at the start of each test and used for comparison to the user's test results. After testing, if the user passes the test, a pass code, date and time are written onto datacard 20 via datacard reader 14.

Each user is preferably equipped with a datacard, preferably a Smart Card, which stores the user's own predetermined baseline. A user's baseline is a measure of the user's normal daily level of alertness and mental fitness. If a user passes a test, a pass code, plus a time and date stamp, is written onto his or her datacard. If a user fails a test, either a failed-test code or no code is written onto the user's card.

Datacard 20 preferably comprises a Smart Card, also known as an Integrated Circuit Card (ICC) or any device wherein an integrated circuit 22 or other compact memory is contained within an identification card. A "memory button", a small memory integrated circuit having an I/O interface and worn or carried by the user may also be utilized. The preferred form factor for Smart Cards is 85.6 mm×53.98 mm×0.76 mm and is the same as the ubiquitous bank card with its magnetic stripe that is used as the payment instrument for numerous financial schemes. The datacard may have contacts or be contactless. A contactless card may contain its own battery, particularly in the case of a "Super Smart Card" which has an integrated keyboard and LCD display. In general however, the operating power is supplied to the contactless card electronics by an inductive loop using low-frequency electro-magnetic radiation. The communications signal may be transmitted in a similar way or can use capacitive coupling or even an optical connection. Most contact cards contain only a simple integrated circuit including a memory portion.

There are preferably at least two types of datacards, permanent and temporary. A pass code is written to a permanent datacard with a time and date stamp, and is erased when the card is used in an access control device. With a temporary datacard, the pass code fades away after a certain period of time, such as five minutes, as determined by the user, the user's employer or any other system administrator. While permanent datacards are less complicated (and therefore less expensive) than their temporary counterparts, the related access control device 30 is more complex since it must contain clocks and the ability to erase a pass code. Likewise, temporary datacards are more complex than permanent cards, but the necessary access control device need not contain clocks or erasing capabilities.

Datacards may also contain a visual indicator of a valid pass code. The least complex are nonindicating datacards, which provide no visual indication of having a valid pass code. A preferred embodiment of the present invention includes indicating datacards which have a visual indicator, such as a glowing or colored spot which indicates the presence or lack of a valid pass code in the datacard. Visual indices allow system administrators to utilize a security guard to check for access control, instead of an electromechanical access control device 30. This will be especially useful in some field operations where it is impractical to use a mechanized gate, turnstile or ignition cutoff. Datacards having visual indices are preferably of the temporary variety, described above, so that the visual indication of a pass code will expire in a short period of time, thereby deterring unauthorized use.

Permanently stored data on data cards preferably includes at least user name, identification number, company, security level, date of hire, testing level, and test type. All of this data is preferably stored only on the datacard, and accessed as needed by reader 14 during original baselining and rebaselining. During baselining, score data, date and time, are preferably retained on the datacards. Once a baseline is calculated, much of this data may be erased from the datacard. Therefore, some data memory registers in integrated circuit 22 are permanent or non-volatile, some temporary (those for baselining), and others, such as pass code, time and date, are erasable by access control device 30.

If a user passes a test, the user preferably removes the datacard from system 10 and moves to an access control switch 30. The access control switch must be opened in order to gain access to the device they will operate or to gain access into a secured area. The user preferably gains access only if he or she inserts datacard 20 into access control switch 30 within a time limit set by the system administrator (nominally five minutes or less). A clock (not shown) in an access control device is preferably set to UCT (Universal Coordinated Time) and determines whether each pass code is valid at the time of review (i.e., whether the pass code is used before expiration). Instead of using a clock in the access control device, the datacard may have a temporary location or storage medium (such as a capacitive switch), enabling the pass code to expire after a predetermined time period has elapsed.

Fundamental screening and baselining of users is preferably accomplished using a basic test to flag users who are significantly below their own normal daily level of alertness and mental fitness. After a group of users utilize the basic test for a predetermined period of time, the system administrator may obtain from the assignee of the present invention, or a licensed developer, a software upgrade. Upgrades may be aimed at testing for particular activity types, provide more stringent screening, or both. Software upgrades are preferably utilized simultaneous with previously installed software, thereby enabling each user to establish a new baseline for the upgrade without losing the use of the baseline established for the previously installed software. After a baseline is established for each user with the upgrade, the system administrator may decide whether users will take a plurality of tests in each test session, or if the previously installed test will be abandoned as soon as each user has a valid baseline for the new test. Another new test can then be introduced. Once a system administrator uses the basic test for a predetermined period of time, such as ninety days or more, other tests which are specific to certain types of jobs or impairments may be used.

The basic test preferably comprises a checkerboard pattern displayed on a display apparatus 15, as illustrated in FIG. 1. Other tests may be based on a board having other than an alternating background pattern, or no background pattern. A plurality of squares of alternating colors (e.g., black and white, as shown) are displayed as a background, while various figures, such as rectangles, triangles, or arrows, are displayed in the white squares in various orientations. The user's task is to press YES when all the shapes are the same, even if the various boxes include the same shape in a variety of orientations, and to otherwise press NO. Other tests may also include more complex figures, or they may include other visual methodologies to test alertness. The inventive tester is intended for nonlinguistic use by people from any nation or linguistic origin. Thus, the screens preferably contain little or no language-based information. Preferably, only nonlinguistic figures, graphics, or pictograms are used.

Normal functional levels of many aspects of psychomotor functions are preferably required from the user to pass the basic test, including visual perception, information processing, focused attention, decision-making, and eye-hand coordination. The basic test is useful for alertness testing because these psychomotor functions represent a person's general alertness and normal functioning and mental fitness. Thus, failing a test indicates that a user's alertness is reduced to a level below their own normal baseline, due to any cause.

A challenge is presented by those users who would purposely attempt to do poorly during the baselining process to enable them to reach a passing score on a later test, even when their alertness is impaired. To address this concern, the basic test preferably includes minimum performance standards applied to all users. Also, a new baselining period preferably begins for each user at the end of time period set by the system administrator, so that those users who would "cheat" the system will gradually move up in performance if they generally make an effort to pass the test on a regular basis.

A test for Alzheimer's Disease dementia on the tester exercises and records the user's response to challenges designed to identify early warnings of the disease. In one embodiment, the test follows current practice, as utilized in paper and pencil tests such as the Mini Mental State Exam or the Janssen Seven Minute Screen, of utilizing both graphic and/or verbal test problems. But, because a computer is utilized instead of a human technician to administer the test, the tests are not subject to subjective scoring and timing inaccuracies. Moreover, where paper and pencil tests are limited to a few parameters regarding test performance, the inventive tester can objectively record numerous performance parameters.

For example, the computer can precisely record the response time and accuracy of response for each test item. The tester can record tremors in hand motion. The tester can then use these results (parameters) to adjust test difficulty to an individual's level of performance during the actual test, and can then present randomized items to prevent the individual from learning the test.

The scoring method utilized by the internal microprocessor in the tester can perform an analysis and display an immediate summary result score. The scoring method will be able to weight response times for each item based on a known difficulty of the item to determine an item score. The scoring method will further compute a weighted average of all scores to determine a summary score result as a single two digit number. Alternatively, the raw data may be downloaded from the portable memory device for individualized analysis.

The tester utilizes the data stored on the data card including historical data to assess relative degree of risk for Alzheimer's or other neurological impairment. In addition, the user may retain the portable memory device containing all test data for further analysis in subsequent testing by other compatible or identical testers. The tester records data in the portable memory device, including data of test, time of test, computed score, actual test performance data (items selected, response times, weighted difficulty of each item, type of item used) test type, portable memory device number, and the history of all previous tests with date and time of and all previously listed test parameters for each test. Additional data stored in the portable memory could include the age, education level, race, sex, language preference, genetic data (including genetic flags for Alzheimer's disease or other genetic predispositions) and other data related to the individual's ability and medical history and medication history, including current drugs being taken.

Analysis of prior baseline results by the risk assessment algorithm incorporated in the tester software allows the tester to establish a historical picture, such as would be shown on a graph where the y-axis reflects computed test score and the x-axis reflects date/time of test, and analyze any change in this performance to determine whether the individual fits within a pattern indicative of possible early Alzheimer's Disease dementia or is within established norms.

For example, mental performance, as based on test performance, will be recorded over a period of years for large numbers of normal individuals and for individuals who have been clinically diagnosed with Alzheimer's Disease. Longitudinal profiles will be developed for normal individuals who subsequently develop dementia. These longitudinal profiles will be stored as mathematical formulas within the risk assessment algorithm. As each individual takes the test over time, he/she develops an individual personal longitudinal profile. This profile will be mathematically compared to the recorded profiles for normal individuals and to the profiles developed for individuals diagnosed with, for example, Alzheimer's disease.

Based on a comparison and statistical analysis of the difference between the individual's profile and the profiles stored in the algorithm, a risk assessment can be made. Individuals taking the test over time will build increasingly detailed and accurate profiles. If the individual is at risk, as indicated, for example, by an individual longitudinal profile that closely follows the profile of other individuals who were subsequently clinically diagnosed with dementia, or can be mathematically projected to follow such a trend, a warning display can be shown by the tester indicating degree of risk and showing instructions regarding contacting an appropriate medical facility for further testing. In this case, an indication of a NO PASS for Alzheimer's Disease dementia would be electronically recorded, with date and time to the individual's portable memory device. In one embodiment, the results are "displayed" in verbal form. For example, the screen on the tester might display the statement, "Your test results show possible impairment of your short term memory performance in a pattern that indicates you could be at risk for early Alzheimer's Disease. Please consult your doctor about this condition." If desired by the user, more detailed data about the user's test performance could be recorded for access later by a medical professional.

A medical facility with on-site portable memory device readers would read the individual's portable memory device during the course of normal or required check ups. An individual with his/her portable memory device marked with the NO PASS indicator would not be given a "pass" in a normal physical exam without further medical testing. The portable memory device thus functions in the same way as the portable memory device with the alertness tester, i.e., to alert appropriate authorities that an individual is at risk. The above description related to alertness testing may be extended to testing for Alzheimer's or the progress of other dementia in a user.

The tester may utilize a variety of software modules, each designed to measure different brain functions. For general alertness, the software measures primarily speed and accuracy of response. For Alzheimer's disease and dementia, the software measures primarily short-term memory performance. A short term memory test, as an indicator of early Alzheimer's disease dementia, may comprise a series of graphic images of ordinary objects shown on the tester screen. The individual being tested is asked to remember the initial group of objects during repetitive presentations of diverse other objects until one of the objects in the initial set is shown again. At this point, the individual should press the appropriate button. Other tests for Alzheimer's could comprise questions shown in verbal form. The individual would be measured for ability to quickly respond to questions about everyday events and to remember words used in ordinary speech. For Parkinson's disease, a different interface may be used whereby the individual being tested will be asked to utilize a joystick or a touchpad to follow a particular path shown on the computer screen. In this case, the computer will measure accuracy, speed, and tremors in hand motion as a characteristic indicator for Parkinson's. The testers may be flexibly adapted to different measurement criteria.

The above description of the medical use for the tester incorporates Alzheimer's disease dementia as the typical use by the tester, but is not limited to measuring impairment related to Alzheimer's disease dementia. For example, utilizing the same system with an alternative touch pad input device to measure movement tremors, the tester could establish baselines and compute risk factors for Parkinson's disease.

The present invention therefore provides an inventive alertness and mental function capability testing apparatus including an adaptive baselining capability and a high level of confidentiality for users' performance and pass/fail information. The tester of the present invention may be used in conjunction with an access guarding device which regulates user-access to machinery or work spaces considered dangerous to operate when below a basic, subjective alertness level. The system may also be easily adapted for use as a performance-level tester, a brain function tester, an awakeness tester, a psycho-motor function tester, or a predictor of future alertness, awakeness, performance, psycho-motor function, or may be applied in testing for diseases affecting mental functioning. Indeed, the term "alertness" as used in the above description may be interchanged with these additional terms while still describing the form and function of the present invention. The inventive system may also be used as an assessor of medical fitness as described in provisional patent application serial No. 60/058,841 cited above. In the medical context, the access control device used in combination with the tester could be a medication dispenser, wherein the type and dosage of medication dispensed will depend on the user's score as recorded on the user's datacard or memory button.

The present invention may be implemented using a conventional general purpose or a specialized digital computer or microprocessor programmed according to the teachings of the present disclosure, as will be apparent to those skilled in the computer art. However, a customized tester device is presently preferred to simplify the user interface and reduce the size of the tester apparatus.

Appropriate software coding can readily be prepared by skilled programmers based on the teachings of the present disclosure, as will be apparent to those skilled in the software art. The invention may also be implemented by the preparation of application specific integrated circuits or by interconnecting an appropriate network of conventional component circuits, as will be readily apparent to those skilled in the art.

The present invention includes a computer program product which is a storage medium (media) having instructions stored thereon/in which can be used to control, or cause, a computer to perform any of the processes of the present invention. The storage medium can include, but is not limited to, any type of disk including floppy disks, mini disks (MD's), optical discs, DVD, CD-ROMs, microdrive, and magneto-optical disks, ROMs, RAMs, EPROMs, EEPROMs, DRAMs, VRAMs, flash memory devices (including flash cards), magnetic or optical cards, nanosystems (including molecular memory ICs), RAID devices, remote data storage/archive/warehousing, or any type of media or device suitable for storing instructions and/or data.

Stored on any one of the computer readable medium (media), the present invention includes software for controlling both the hardware of the general purpose/specialized computer or microprocessor, and for enabling the computer or microprocessor to interact with a human user or other mechanism utilizing the results of the present invention. Such software may include, but is not limited to, device drivers, operating systems, and user applications. Ultimately, such computer readable media further includes software for performing the present invention, as described above.

Included in the programming (software) of the general/specialized computer or microprocessor are software modules for implementing the teachings of the present invention, including, but not limited to, presenting tests, recording parameters, including times and movements (including tremors), analyzing test results, computing historical averages and baselines, maintaining running averages, comparing parameters and other results to historical averages and baselines, and the display, storage, or communication of results according to the processes of the present invention.

Obviously, numerous modifications and variations of the present invention are possible in light of the above teachings. It is therefore to be understood that within the scope of the appended claims, the invention may be practiced otherwise than as specifically described herein.

What is claimed is:

1. A method of assessing mental function of a user, comprising the steps of:

testing a current mental function capability of a user;

comparing the current mental function capability of said user with a baseline mental function capability of the user; and displaying a result of the comparison;

wherein said steps of testing, comparing, and displaying are initiated upon insertion of a portable memory device into a testing device configured to perform said steps.

2. The method according to claim 1, wherein said portable memory device is a smart card.

3. The method according to claim 1, wherein said step of comparing comprises performing a statistical analysis of the current mental function capability of said user with previous mental function tests of said user stored on the portable memory device.

4. The method according to claim 1, wherein said step of comparing comprises comparing a current mental function capability and previous mental function capabilities of the user stored on the portable memory device to at least one predetermined mental function capability pattern.

5. The method according to claim 1, wherein said at least one predetermined mental function capability is at least one of an Alzheimer's degradation pattern, a Parkinson's degradation patter, and a normal aging pattern.

6. The method according to claim 1, wherein said baseline mental function capability comprises longitudinal data regarding historical mental function capabilities of the user.

7. The method according to claim 1, wherein said step displaying comprises providing said result in visual form as text or graphics.

8. The method according to claim 1, wherein said baseline mental function capability is determined by the steps of:

testing the user with a mental function capability test; and storing results of the mental function capability test as said baseline.

9. The method according to claim 8, wherein said step of testing the user with a mental function capability test comprises:

testing the user with multiple individual mental function capability tests; and combining results of each individual test into a single result to be stored as said baseline.

10. The method according to claim 9, wherein said step of combining comprises at least one of averaging, determining a median, or other statistical analysis of the results of each individual test.

11. The method according to claim 8, wherein said mental function capability test is non-linguistic test with graphic or textual instructions.

12. The method according to claim 11, wherein said non-linguistic test includes testing for visual perception, information processing, focused attention, decision making, and eye-hand coordination.

13. The method according to claim 8, wherein said mental function test is at least one of Mini Mental State Exam, Janssen Seven Minute Screen, other Alzheimer's Disease/Dementia test, or a test for other mental impairments such as Parkinson's Disease.

14. The method according to claim 1, wherein said step of testing a current mental function capability comprises:
   testing the user using a test or method that is the same or similar to that used in determining said baseline.

15. The method according to claim 1, wherein said step of testing a current mental function capability includes the steps of:
   communicating a mental function test having test items to said user;
   recording all parameters for each of the test items contained in the mental function test; and
   utilizing the recorded parameters to determine the current mental function capability of said user.

16. The method according to claim 15, wherein:
   said test items include groups of test items; and
   the recorded parameters for each group provide a measure of at least one brain function.

17. The method according to claim 15, wherein said test items include a group of test items for testing at least one of short term memory and other Alzheimer's dementia indicators.

18. The method according to claim 15, wherein said test items include at least one psychomotor test.

19. The method according to claim 15, wherein said parameters include at least one of speed of response and accuracy of response.

20. The method according to claim 15, wherein said test items include a group of test items configured to test Parkinson's disease risk factors.

21. The method according to claim 1, further comprising the step of:
   maintaining historical data with respect to each mental function test performed by the user.

22. The method according to claim 1, wherein said step of testing a current mental function capability of the user includes measurement of tremors.

23. The method according to claim 22, wherein said measurement of tremors includes the measurement of tremors transmitted from said user through an input touchpad or other input device.

24. The method according to claim 1, wherein said step of displaying a result comprises:
   displaying a pass if the current mental functioning capability is at or near the user's baseline mental function capability.

25. The method according to claim 1, wherein said step of comparing comprises computing a mathematical analysis of the user's current mental function capability by comparison to a historical record of performance as maintained in said baseline.

26. The method according to claim 25, further comprising the step of:
   determining a degree of risk for Alzheimer's Disease based on said mathematical analysis; and
   outputting the results of at least one of said degree of risk and said mathematical analysis.

27. The method according to claim 26, wherein said step of outputting comprises displaying the results on a display device.

28. The method according to claim 26, further comprising the step of storing at least one of the tested current mental function capability of said user, results of said mathematical analysis, and the Alzheimer's risk computed on the portable memory device.

29. The method according to claim 1, further comprising the step of:
   writing the results of said current mental functioning test to the portable memory device;
   wherein the step of displaying comprises writing the results of said comparison to a device that displays a visual indicator to notify health care personnel of a status of the user's mental function capability.

30. The method according to claim 1, further comprising the step of updating said baseline with results from the current mental function test.

31. The method according to claim 1, further comprising the steps of:
   purchasing the portable memory device from a display rack or vending machine;
   inserting the portable memory device into a read/write device for performing said method; and
   writing results of at least one of said current mental function capability and said comparison to the portable memory device.

32. The method according to claim 31, wherein the portable memory device includes a descriptive file of information for said user, including information on any of Alzheimer's disease, Parkinson's disease, or other impairments.

33. The method according to claim 32, wherein said descriptive file is printed materials.

34. The method according to claim 32, wherein said descriptive file is includes any of normal, average, or median test scores for performing said method.

35. The method according to claim 1, wherein:
   said portable memory device contains said baseline; and
   said method further comprises the step of writing at least one of said current mental functioning, said results and raw response to said testing to the portable memory device.

36. The method according to claim 1, further comprising the step of inserting the portable memory device into said testing device.

37. The method according to claim 1, wherein said step of testing a current mental function comprises reading user responses to test items via at least one of buttons, keyboard, touch pad, mouse, joystick, or other user input device.

38. The method according to claim 1, wherein said step of testing a current mental function of said user includes the steps of:
   displaying a series of images; and
   retrieving user responses to the displayed images.

39. The method according to claim 38, wherein:
   said images comprise at least one of graphic screens, graphic patterns, colored patterns, verbal questions, or other items; and
   said images, individually or in combination, are designed such that responses to said images are a measure of particular parameters of mental performance.

40. The method according to claim 1, wherein said step of testing a current mental function of a user comprises testing said user with a test for Alzheimer's disease or other neurological impairment.

41. A system for assessing alertness of a user, the system comprising:

a microprocessor;

a visual display apparatus in electrical communication with said microprocessor;

a data I/O port in electrical communication with said microprocessor;

a portable data storage device having a user data memory, the portable data storage device being releasably interfaceable with said data I/O port, thereby enabling data downloading to and data uploading from said microprocessor;

a test memory in electrical communication with said microprocessor, said test memory being loaded with at least one executable software program comprising an Alzheimer's or other dementia test and a baseline data set, the test comprising test information displayed on said visual display; and an input mechanism in electrical communication with said microprocessor for receiving input data from a user in response to said test information displayed on said visual display;

wherein, upon insertion of the portable storage device into said data I/O port, said microprocessor is enabled to execute said software program, receive said test information from said test memory, display said test information on sid visual display, receive said input data from the user via said input mechanism, compare said input data to said baseline data set, assign either of a selected test performance-pass or a test performance-fail signal to said user depending upon the result of said comparison, and forward said selected signal to said portable data storage device.

42. A method of assessing mental function of a user, comprising the steps of:

testing a current mental function capability of a user;

reading historical data regarding previous mental function capabilities of the user from a smart card type portable storage device;

comparing the current mental function capability of said user with the historical data;

displaying a result of the comparison; and writing the current mental function capability of the user in said historical data on the smart card type portable storage device.

43. A method of assessing mental function of a user, comprising the steps of:

testing a current mental function capability of a user;

comparing the current mental function capability of said user with a baseline mental function capability of the user; and displaying a result of the comparison;

wherein said steps of testing comprises testing the user using one of a Mini Mental State Exam and Janssen Seven Minute Screen.

44. A method of assessing mental function of a user, comprising the steps of:

testing a current mental function capability of a user;

comparing the current mental function capability of said user with a baseline mental function capability of the user; and writing a result of the test to a portable memory device having a display capability; and displaying the result of the test on the portable memory device.

45. A testing device for assessing mental function of a user, comprising:

a user interface having a display for presenting mental tests to a user and user input devices configured to receive user responses;

a data port configured to accept a portable memory device;

a processing unit configured to control the user interface and read/write to the data port; and a computer readable media coupled to the processing unit and storing instructions that cause the processing unit to recognize insertion of a portable memory device into said data port, and, after recognition of the portable memory device, perform a test of the user's current mental function capability, and then display a result of the test.

46. The testing device according to claim 45, wherein said test of the user's current mental function capability comprises testing a mental function capability of the user, reading a baseline mental function capability of the user from the portable memory device, and comparing the user's current mental function capability to the baseline to determine said result.

47. The testing device according to claim 46, wherein said test of the user's current mental function capability further comprises writing at least one of the user's current mental function capability and said result to the portable memory device.

48. The testing device according to claim 45, wherein said dataport is a smart card reader.

* * * * *